United States Patent
Roesler et al.

[11] Patent Number: 6,046,270
[45] Date of Patent: *Apr. 4, 2000

[54] SILANE-MODIFIED POLYURETHANE RESINS, A PROCESS FOR THEIR PREPARATION AND THEIR USE AS MOISTURE-CURABLE RESINS

[75] Inventors: Richard R. Roesler, Wexford, Pa.; Lutz Schmalstieg, Cologne, Germany

[73] Assignees: Bayer Corporation, Pittsburgh, Pa.; Bayer Aktiengesellschaft, Leverkusen, Germany

[*] Notice: This patent is subject to a terminal disclaimer.

[21] Appl. No.: 09/172,750

[22] Filed: Oct. 14, 1998

[51] Int. Cl.$^7$ .................. C08J 3/00; C08K 3/20; C08L 75/00; C08L 83/00; C08G 18/00
[52] U.S. Cl. .................. 524/590; 524/588; 524/589; 528/28; 528/44; 528/60; 528/85
[58] Field of Search .................. 524/588, 589, 524/590; 528/28, 44, 60, 85

[56] References Cited

U.S. PATENT DOCUMENTS

| | | | |
|---|---|---|---|
| 3,420,800 | 1/1969 | Haggis | 260/75 |
| 3,567,692 | 3/1971 | Haggis | 260/75 |
| 4,067,844 | 1/1978 | Barron et al. | 260/37 N |
| 4,625,012 | 11/1986 | Rizk et al. | 528/28 |
| 5,162,426 | 11/1992 | Hazan et al. | 524/521 |
| 5,364,955 | 11/1994 | Zwiener et al. | 556/418 |
| 5,766,751 | 6/1998 | Kotani et al. | 428/323 |

*Primary Examiner*—Patrick D. Niland
*Attorney, Agent, or Firm*—Joseph C. Gil; Thomas W. Roy

[57] ABSTRACT

The present invention relates to moisture-curable resins having an alkoxysilane group content (calculated as Si, MW 28) of 0.2 to 4.5% by weight, based on the weight of the moisture-curable resins, and optionally containing hydroxy groups, wherein the alkoxysilane groups are incorporated as the reaction products at an NCO/OH equivalent ratio of 0.5:1.0 to 1.0:1.0 of i) a polyol having a functionality of at least 4 and an equivalent weight of at least 200 with ii) a compound containing urea, isocyanate and alkoxysilane groups corresponding to the formula I

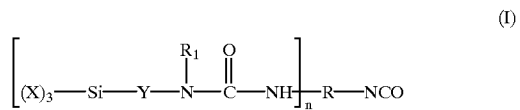

The present invention also relates to a process for preparing these moisturecurable resins, to coating, adhesive or sealing compositions containing these resins as the binder and to the compounds containing urea, isocyanate and alkoxysilane groups used to prepare these resins.

20 Claims, No Drawings

SILANE-MODIFIED POLYURETHANE RESINS, A PROCESS FOR THEIR PREPARATION AND THEIR USE AS MOISTURE-CURABLE RESINS

BACKGROUND OF THE INVENTION

1. Field of the Invention

The present invention relates to moisture-curable resins containing alkoxysilane groups and optionally hydroxy groups, which can be cured in the presence of moisture to form coatings, adhesives and sealants, to a process for their production and to the compounds containing urea, isocyanate and alkoxysilane groups used to prepare the moisture-curable resins.

2. Description of the Prior Art

It is known that polyisocyanate resins are curable in the presence of atmospheric moisture to form polyurea coatings. During the curing mechanism an isocyanate group reacts with moisture to form an amino group, which then reacts with another isocyanate group to form a urea. One of the disadvantages of these moisture-curable resins is that the curing mechanism is relatively slow.

It has been suggested in U.S. Pat. Nos. 3,420,800 and 3,567,692 that the curing rate of moisture-curable polyisocyanates can be increased by incorporating either aldimines or ketimines. It is stated that the reaction of moisture with an aldimine or ketimine to form the corresponding amine is faster than the reaction of moisture with an isocyanate group to form an amine. A disadvantage of the use of aldimines and ketimines to accelerate the cure of polyisocyanates is that it requires the preparation of an additional component and requires some type of metering equipment to ensure that the two components are blended in the proper proportions.

Accordingly, there is a need to provide moisture-curable resins that do not require a co-reactant. Such resins have been disclosed in U.S. Pat. No. 5,364,955 and U.S. Pat. No. 5,766,751, which describe silane-terminated resins that have been prepared by reacting NCO prepolymers with silane aspartates to form either urea or hydantoin groups. The silane aspartates are prepared by initially reacting amino-functional silanes with maleic or fumaric acid esters. The silane aspartates are then reacted with NCO prepolymers to form the moisture-curable resins.

One of the disadvantages of this process is that it is not possible to prepare the silane-containing resins from higher functional polyols. When these polyols are reacted with polyisocyanates, primarily diisocyanates, gelation often occurs due to chain extension, even at NCO/OH equivalent ratios of 2:1.

U.S. Pat. No. 5,162,426 discloses the reaction of isocyanatoalkyl trialkoxysilanes with hydroxy-functional ethylenically unsaturated monomers and the subsequent polymerization of these unsaturated monomers with other unsaturated monomers to form silane-functional polymers. A disadvantage of these resins is the cost of the isocyanatoalkyl trialkoxysilanes.

Accordingly, it is an object of the present invention to provide silane-containing resins based on high functionality polyols, which do not suffer from the disadvantages of the prior art.

This object may be achieved with the moisture-curable resins according to the present invention and the process for their production, which are described in more detail hereinafter.

SUMMARY OF THE INVENTION

The present invention relates to moisture-curable resins having an alkoxysilane group content (calculated as Si, MW 28) of 0.2 to 4.5% by weight, based on the weight of the moisture-curable resins, and optionally containing hydroxy groups, wherein the alkoxysilane groups are incorporated as the reaction products at an NCO/OH equivalent ratio of 0.5:1.0 to 1.0:1.0 of i) a polyol having a functionality of at least 4 and an equivalent weight of at least 200 with ii) a compound containing urea, isocyanate and alkoxysilane groups corresponding to the formula I

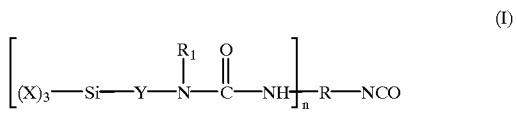

wherein

X represents identical or different organic groups which are inert to isocyanate groups below 100° C., provided that at least one of these groups is an alkoxy group, Y represents a linear or branched alkylene radical containing 1 to 8 carbon atoms, R represents the residue obtained by removing the isocyanate groups from a monomeric polyisocyanate or a polyisocyanate adduct containing n+1 isocyanate groups, $R_1$ represents an organic group which is inert to isocyanate groups at a temperature of 100° C. or less and n is an integer from 1 to 3.

The present invention also relates to a process for preparing these moisture-curable resins, to coating, adhesive or sealing compositions containing these resins as the binder and to the compounds containing urea, isocyanate and alkoxysilane groups used to prepare these resins.

DETAILED DESCRIPTION OF THE INVENTION

To prepare the moisture-curable resins according to the present invention high functionality polyols are reacted with compounds containing isocyanate, urea and alkoxysilane groups. The latter compounds may be prepared by reacting a polyisocyanate with an amino-functional alkoxysilane to form a compound containing one isocyanate group and one or more urea and alkoxysilane groups.

The moisture-curable resins have a) an alkoxysilane group content (calculated as Si, MW 28) of 0.2 to 4.5% by weight, preferably 0.2 to 4% and more preferably 0.5 to 3.5%, and b) optionally a hydroxy group content (calculated as OH, MW 17) of less than 2% by weight, preferably less than 1% by weight and more preferably less than 0.2% by weight.

Suitable compounds containing isocyanate, urea and alkoxysilane groups, which may be used to prepare the moisture-curable resins, include those corresponding to formula I wherein X represents identical or different organic groups which are inert to isocyanate groups below 100° C., provided that at least one of these groups is an alkoxy group, preferably alkyl or alkoxy groups having 1 to 4 carbon atoms and more preferably alkoxy groups, Y represents a linear or branched alkylene radical containing 1 to 8 carbon atoms, preferably a linear radical containing 2 to 4 carbon atoms or a branched radical containing 5 to 6 carbon atoms, more preferably a linear radical containing 3 carbon atoms, R represents the residue obtained by removing the isocyanate groups from a monomeric polyisocyanate or a polyisocyanate adduct containing n+1 isocyanate groups, preferably a monomeric polyisocyanate, more preferably a monomeric diisocyanate and most preferably a monomeric diisocyanate containing aliphatically and/or cycloaliphatically bound isocyanate groups, $R_1$ represents an organic group which is inert to isocyanate groups at a temperature of 100° C. or less, preferably an alkyl, cycloalkyl or aromatic group having 1 to 12, preferably 1 to 8 carbon atoms, or $R_1$ may also represent a group corresponding to formula II

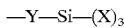  (II)

and n is an integer from 1 to 3, preferably 1 or 2 and more preferably 1.

Especially preferred are compounds in which X represents methoxy, ethoxy groups or propoxy groups, more preferably methoxy or ethoxy groups and most preferably methoxy groups.

Suitable compounds containing alkoxysilane groups and amino groups, which may be used to prepare the compounds of formula I, are those corresponding to formula III wherein

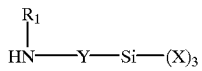  (III)

wherein X, Y, $R_1$ and n are as previously defined.

Examples of suitable aminoalkyl alkoxysilanes corresponding to formula IV containing secondary amino groups include N-phenylaminopropyl-trimethoxysilane (available as A-9669 from OSI Specialties, Witco), bis-(γ-trimethoxysilylpropyl)amine (available as A-1170 from OSI Specialties, Witco), N-cyclohexylaminopropyltriethoxysilane, N-methylaminopropyl-trimethoxysilane and the corresponding alkyl diethyoxy and alkyl dimethoxy silanes.

Especially preferred compounds containing isocyanate, urea and alkoxysilane groups are those corresponding to the formula IV

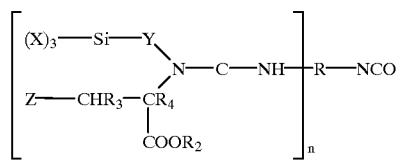  (IV)

wherein X, Y, R and n are previously defined and

Z represents $COOR_5$ or an aromatic ring, preferably $COOR_5$, $R_2$ and $R_5$ are identical or different and represent organic groups which are inert to isocyanate groups at a temperature of 100° C. or less, preferably alkyl groups having 1 to 9 carbon atoms, more preferably methyl, ethyl or butyl groups and $R_3$ and $R_4$ are identical or different and represent hydrogen or organic groups which are inert to isocyanate groups at a temperature of 100° C. or less, preferably hydrogen.

The compounds of formula IV are prepared by reacting polyisocyanates with compounds corresponding to formula V

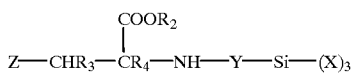  (V)

wherein X, Y, Z, R, $R_2$, $R_3$, $R_4$, $R_5$ and n are as previously defined.

The compounds of formula V are prepared by reacting aminoalkyl alkoxysilanes corresponding to formula VI $H_2N-Y-Si-(X)_3$  (VI)

wherein X and Y are as previously defined, with maleic, fumaric or cinnamic acid esters corresponding to formula VII $Z-CR_3=CR_4-COOR_2$  (VII).

Examples of suitable aminoalkyl alkoxysilanes of formula VI include 2-aminoethyl-dimethylmethoxy-silane; 6-aminohexyl-tributoxysilane; 3-aminopropyl-trimethoxysilane; 3-aminopropyl-triethoxysilane; 3-aminopropyl-methyldiethoxysilane; 5-aminopentyl-trimethoxysilane; 5-aminopentyl-triethoxysilane, 3-aminopropyl-triisopropoxysilane and 4-amino-3,3-dimethylbutyidimethoxymethylsilane. 4amino-3,3dimethylbutyidimethoxy-methylsilane is preferred and 3-aminopropyltrimethoxysilane and 3-aminopropyl-triethoxysilane are especially preferred.

Examples of optionally substituted maleic, fumaric or cinnamic acid esters suitable for use in the preparation of the polyaspartates include dimethyl, diethyl, dibutyl (e.g., di-n-butyl), diamyl, di-2-ethylhexyl esters and mixed esters based on mixture of these and/or other alkyl groups of maleic acid and fumaric acid; the methyl, ethyl and butyl esters of cinnamic acid; and the corresponding maleic, fumaric and cinnamic acid esters substituted by methyl in the 2- and/or 3-position. The dimethyl, diethyl and dibutyl esters of maleic acid are preferred and the diethyl and dibutyl esters are especially preferred.

The reaction of primary amines with maleic, fumaric or cinnamic acid esters to form the aspartates of formula V is known and described, e.g. in U.S. Pat. No. 5,364,955, which is herein incorporated by reference. The preparation of the aspartates may be carried out, for example, at a temperature of 0 to 100° C. using the starting materials in such proportions that at least 1, preferably 1, olefinic double bond is present for each primary amino group. Excess starting materials may be removed by distillation after the reaction. The reaction may be carried out with or without a solvent, but the use of a solvent is less preferred. If a solvent is used, dioxane is an example of a suitable solvent. The compounds of formula V are colorless to pale yellow. They may be reacted with polyisocyanate monomers and/or adducts to form the compounds containing isocyanate, urea and alkoxysilane groups without further purification.

Suitable polyisocyanates for preparing the compounds containing isocyanate, urea and alkoxysilane groups are selected from monomeric diisocyanates and polyisocyanate adducts having an average functionality of 2 to 4, preferably 2.

Suitable monomeric diisocyanates may be represented by the formula

wherein R is as previously defined. The monomeric polyisocyanates have a molecular weight of about 112 to 1,000, preferably about 140 to 400 and include those in which R represents a divalent aliphatic hydrocarbon group having 4 to 40, preferably 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 1,6-hexamethylene diisocyanate, 2,2,4trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methylcyclohexyl)-methane, α,α,α',α'-tetramethyl-1,3- and/or -1,4-xylylene diisocyanate, 1-isocyanato-1-methyl-4 (3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenylmethane diisocyanate, 1,5-diisocyanato naphthalene and mixtures thereof.

Polyisocyanates containing 3 or more isocyanate groups such as 4-isocyanantomethyl-1,8-octamethylene diisocyanate and aromatic polyisocyanates such as 4,4',4"-triphenylmethane triisocyanate and polyphenyl polymethylene polyisocyanates obtained by phosgenating aniline/formaldehyde condensates may also be used.

Preferred organic diisocyanates include 1,6-hexamethylene diisocyanate, 1-isocyanato-3-isocyanatomethyl-3,5,5-trimethylcyclohexane (isophorone diisocyanate or IPDI), bis-(4-isocyanatocyclohexyl)-methane, 1-isocyanato-1-methyl-4(3)-isocyanatomethyl cyclohexane, 2,4- and/or 2,6-toluylene diisocyanate, and 2,4- and/or 4,4'-diphenyl-methane diisocyanate.

In accordance with the present invention the polyisocyanate component may also be present in the form of a polyisocyanate adduct. Suitable polyisocyanate adducts are those containing isocyanurate, uretdione, biuret, urethane, allophanate, carbodiimide and/or oxadiazinetrione groups, such as those disclosed in U.S. Pat. No. 5,668,238, herein incorporated by reference.

Preferred polyisocyanate adducts are the polyisocyanates containing isocyanurate groups, biuret groups, allophanate groups and/or uretdione groups, especially those prepared from the preferred monomeric diisocyanates.

Suitable polyols for preparing the moisture-curable resins according to the invention have an average hydroxy functionality of at least 4, preferably 4 to 200 and more preferably 7 to 100, and an equivalent weight (determined by end group analysis) of at least 200, preferably 200 to 5000, more preferably 200 to 2500 and most preferably 200 to 1000.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyacrylate polyols, polyester polyols, polyether polyols and polyhydroxy polycarbonates are preferred, especially the polyacrylate polyols.

To obtain the required hydroxy functionalities it is necessary to use starting materials having functionalities greater than 2 to prepare the polycondensation polymers. Preferably, the compounds having these higher functionalities are the low molecular weight alcohols used to prepare these polymers. Examples include trimethylol propane, 1,2,6-hexanetriol, 1,2,4-butanetriol, trimethylol ethane, pentaerythritol, mannitol, sorbitol and sucrose. Polyethers which have been obtained by the reaction of starting compounds containing amino groups can also be used, but are less preferred for use in the present invention. Suitable amine starting compounds include ethylene diamine, diethylene triamine and triethylene tetraamine.

Examples of suitable high molecular weight polyhydroxyl compounds include polyester polyols prepared from low molecular weight alcohols and polybasic carboxylic acids such as adipic acid, sebacic acid, phthalic acid, isophthalic acid, tetrahydrophthalic acid, hexahydrophthalic acid, maleic acid, the anhydrides of these acids and mixtures of these acids and/or acid anhydrides. Polylactones having hydroxyl groups, particularly poly-ε-caprolactone, are also suitable for producing the prepolymers.

Also suitable for preparing the moisture-curable resins are polyether polyols, which may be obtained in known manner by the alkoxylation of suitable starter molecules. Examples of suitable starter molecules include the known diols and higher functional alcohols, water, organic polyamines having two or more N—H bonds and mixtures thereof. Suitable alkylene oxides for the alkoxylation reaction are preferably ethylene oxide and/or propylene oxide, which may be used in sequence or in admixture.

Other suitable polyols include polycarbonates having hydroxyl groups, which may be produced by the reaction of diol and higher functionality alcohols with phosgene or diaryl carbonates such as diphenyl carbonate.

Further details concerning the low molecular weight compounds and the starting materials and methods for preparing the high molecular weight polyhydroxy compounds are disclosed in U.S. Pat. No. 4,701,480, herein incorporated by reference.

Other examples include the known high molecular weight amine-functional compounds, which may be prepared by converting the terminal hydroxy groups of the polyols previously described to amino groups, and the high molecular weight polyaspartates and polyaldimines disclosed in U.S. Pat. No. 5,243,012 and 5,466,771, respectively, herein incorporated by reference.

The moisture-curable resins are preferably prepared in two stages. In the first stage the compounds containing isocyanate, urea and alkoxysilane groups are prepared by reacting a polyisocyanate with an amino-functional alkoxysilane to form a compound containing one isocyanate group and one or more alkoxysilane groups. To ensure that the products contain one isocyanate group, the number of equivalents of amino groups is one less than the number of equivalents of isocyanate groups. For example, one mole of triisocyanate is reacted with two moles of aminosilane and one mole of diisocyanate is reacted with one mole of aminosilane.

When diisocyanates are used as the starting material, it is possible to react an excess of the diisocyanate and to subsequently remove any unreacted diisocyanate by distillation in known manner. Even when one mole of diisocyanate is reacted with one mole of aminosilane, unreacted diisocyanate may be present; however, the unreacted diisocyanate may be removed by distillation.

In accordance with the present invention the special type of urea groups formed by the reaction of the amino-functional compounds containing alkoxysilane groups and aspartate groups (i.e., those corresponding to formula V) with the polyisocyanate component may be converted to hydantoin groups in known manner by heating the compounds at elevated temperatures, optionally in the presence of a catalyst. Therefore, the term "urea groups" is also intended to include other compounds containing the group, N—CO—N, such as hydantoin groups.

If it is desired to convert the urea groups to hydantoin groups, it is preferred to form the hydantoin groups after the formation of the moisture-curable resins in accordance with the second stage of the two-stage process. This is because during the formation of the hydantoin groups, a monoalcohol is given off which can react with the isocyanate group of the compounds containing isocyanate, urea and alkoxysilane groups. This reaction prevents the isocyanate groups from being available for reaction with the high functionality polyols in the second stage of the two-stage process.

The moisture-curable resins are obtained in the second stage by reacting the compounds containing one isocyanate group and one or more alkoxysilane groups with the high functionality polyol at an NCO/OH equivalent ratio of 0.5:1.0 to 1.0:1.0, preferably 0.7:1.0 to 1.0:1.0 and more preferably 0.95:1.0 to 1.0:1.0.

The first stage reaction to form the urea groups is conducted at a temperature of 10 to 120° C., preferably 20 to 100° C. and more preferably 40 to 80° C., while the second stage reaction, which forms urethane groups, is conducted at a temperature of 20 to 150° C., preferably 50 to 120° C. and more preferably 60 to 100° C.

The compounds of the present invention are suitable for use in one-component, coating, adhesive or sealing compositions, which can be cured in the presence of atmospheric moisture by "silane polycondensation" from the hydrolysis of alkoxysilane groups to form Si—OH groups, which subsequently react to form siloxane groups (Si—O—Si).

Suitable metallic, acidic or basis catalysts may be used to promote the curing reaction. Examples include acids such as paratoluene sulfonic acid; metallic salts such as dibutyl tin dilaurate; tertiary amines such as triethylamine or triethylene diamine; and mixtures of these catalysts. Low molecular weight, basic aminoalkyl trialkoxysilanes, such as those represented by formula IV, also accelerate hardening of the compounds according to the invention.

The one-component compositions generally have a solids content of 30 to 80%, preferably 40 to 60%, based on the weight of the one-component composition. Suitable organic solvents include those which are known from polyurethane chemistry.

The compositions may also contain known additives, such as leveling agents, wetting agents, flow control agents, antiskinning agents, antifoaming agents, fillers (such as silica, aluminum silicates and high-boiling waxes), viscosity regulators, plasticizers, pigments, dyes, UV absorbers and stabilizers against thermal and oxidative degradation.

The one-component compositions may be applied to any desired substrates, such as wood, plastics, leather, paper, textiles, glass, ceramics, plaster, masonry, metals and concrete. They may be applied by standard methods, such as spray coating, spread coating, flood coating, casting, dip coating, roll coating. The coating compositions may be clear or pigmented.

The one-component compositions may be cured at ambient temperature, or at elevated temperatures of 50 to 150° C., preferably 60 to 100° C. Preferably, the moisture-curable resins are cured at ambient temperatures.

The invention is further illustrated but is not intended to be limited by the following examples in which all parts and percentages are by weight unless otherwise specified.

EXAMPLES

Silane Aspartate 1—N-(3-Trimethoxysilylpropyl) Aspartic Acid Diethyl Ester 1483 parts (8.27 equiv.) of 3-aminopropyltrimethoxysilane were added to a 5 liter flask fitted with agitator, thermocouple, nitrogen inlet and addition funnel with condenser. 1423.2 parts (8.27 equiv.) of diethyl maleate were added dropwise over a period of 2 hours. The temperature of the reactor was maintained at 25° C. during the addition. The reactor was maintained at 25° C. for an additional 5 hours at which time the product was poured into glass containers and sealed under a blanket of nitrogen. After one week the unsaturation number was 0.6 indicating the reaction was ~99% complete. The product, N-(3-trimethoxysilylpropyi) aspartic acid diethyl ester, had a viscosity of 11 mPa.s at 25° C.

Acrylic Polyol I

A polyacrylate polyol having an OH equivalent weight of 415, a functionality of about 95, an OH content of 4.1 % and an acid number of <10, and prepared from 40.5% styrene, 31.4% hydroxyethyl methacrylate, 23.7% butylacrylate, 0.9% acrylic acid and 3.5% di-tert.-butyl peroxide.

Polyester Polyol I

A polyester polyol having an OH equivalent weight of 770, an OH content of 2.2% and a functionality of about 5, and prepared from 41.2% trimethylol propane, 10.8% adipic acid, 28.5% hexahydrophthalic anhydride and 19.5% 2-ethyl hexanoic acid.

Polyol 1

A polyacrylatelpolyester polyol mixture having an OH equivalent weight of 500, a functionality of about 65, an OH content of 3.40% and an acid number of <10, present as a 70% solution in butyl acetate, and containing 42% of acrylic polyol I and 28% of polyester polyol I.

Example 1—Preparation of Moisture-Curable Resin 1

222.0 parts (2.0 equiv.) of isophorone diisocyanate were charged at ambient temperature to a reaction flask fitted with an agitator, thermocouple, nitrogen inlet, and addition funnel with condenser. 366.6 parts (1 equiv.) of silane asparate 1 was added to the reaction flask through the addition funnel to control the exotherm for the formation of urethane groups by maintaining the reaction temperature below 30°. The addition was complete after one hour and fifteen minutes. The reaction mixture was heated to 60° C. and then 561.8 parts of polyol 1 were added to the reaction mixture followed by stirring for two hours until no isocyanate groups could be detected by IR. After cooling 252.2 parts of butyl acetate were added to give a final solids content of 70% and a viscosity of 6300 mPa.s at 25° C.

Example 2—Preparation of Moisture-Curable Resin 2

168.0 parts (2.0 equiv.) of 1,6-hexamethylene diisocyanate were charged at ambient temperature to a reaction flask fitted with an agitator, thermocouple, nitrogen inlet, and addition funnel with condenser. 366.6 parts (1 equiv.) of silane asparate 1 was added to the reaction flask through the addition funnel to control the exotherm for the formation of urethane groups by maintaining the reaction temperature below 30°. The addition was complete after one hour and fifteen minutes. The reaction mixture was heated to 60° C. and then 561.8 parts of polyol 1 were added to the reaction mixture followed by stirring for two hours until no isocyanate groups could be detected by IR. After cooling 229.1 parts of butyl acetate were added to give a final solids content of 70% and a viscosity of 7700 mPa.s at 25° C.

Example 3—Preparation of Moisture-Curable Resin 3

132.0 parts (1.0 equiv.) of bis-(4-isocyanatocyclohexyl)-methane were charged at ambient temperature to a reaction flask fitted with an agitator, thermocouple, nitrogen inlet, and addition funnel with condenser. 183.3 parts (0.5 equiv.) of silane asparate 1 was added to the reaction flask through the addition funnel to control the exotherm for the formation of urethane groups by maintaining the reaction temperature below 30°. The addition was complete after one hour and fifteen minutes. The reaction mixture was heated to 60° C. and then 280.9 parts of polyol 1 were added to the reaction mixture followed by stirring for two hours until no isocyanate groups could be detected by IR. After cooling 135.2 parts of butyl acetate were added to give a final solids content of 70%. The solution appeared to be a rubbery solid which did not flow.

Example 4—(Comparison) Preparation of an NCO Prepolymer 280 parts (0.5 equiv) of polyol 1 and 126 parts of butyl acetate solvent were charged to a round bottom flask fitted with stirrer, thermometer, nitrogen inlet and addition funnel. 111 parts (1.0 eq) of isophorone diisocyanate were added through the addition funnel over a three hour period while maintaining the reaction at 25° C. to maximize the differential reactivity between the two isocyanate groups of isophorone diisocyanate. After the addition was complete the reaction was maintained at 25° C. for an additional five hours when the isocyanate content by titration was found to be 6.93% (theor. 4.06%). The reaction mixture gelled after storage for 96 hours at room temperature. No silane aspartate was added.

Example 5—(Comparison) Preparation of an NCO Prepolymer 55 parts (0.5 eq) of isophorone diisocyanate were charged to a round bottom flask fitted with stirrer, thermometer, nitrogen inlet and addition funnel. The reaction was maintained at 25° C. to maximize the differential reactivity between the two isocyanate groups of isophorone diisocyanate. 140 parts (0.25 equiv) of polyol 1 and 63 parts of butyl acetate solvent were added through the addition funnel over a one hour period while maintaining the reaction at 25° C. to maximize the differential reactivity between the two isocyanate groups of isophorone diisocyanate. After the addition was complete the reaction was maintained at 25° C. for an additional 6.5 hours. The reaction mixture gelled after 14 hours storage at room temperature. No silane aspartate was added.

The preceding comparison examples demonstrate the need to prepare the silane-terminated resins by initially reacting the isocyanate component with the silane aspartate to form an intermediate containing isocyanate and silane aspartate groups, which is subsequently reacted with the high functionality polyol to form the moisture-curable resin. This procedure is demonstrated in the examples according to the invention.

The attempts to prepare these compounds by initially reacting the isocyanate component with the high functionality polyol to form an NCO prepolymer and subsequently reacting the prepolymer with the silane asparate were unsuccessful.

Preparation of a Film From Moisturecurable Resin 1

Coated panels were prepared by adding one part of a 50:50 mixture of dimethyl tin diacetate and diazobicyclooctane to 100 parts of moisturecurable resin 1. The resin was cast as a 5 mil wet film which resulted in an approximately 3.5 mil dry film. The coating was tack free in two hours and had an F pencil hardness after one week.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A moisture-curable resin having an alkoxysilane group content (calculated as Si, MW 28) of 0.2 to 4.5% by weight, based on the weight of the moisture-curable resin, and optionally containing hydroxy groups, wherein the alkoxysilane groups are incorporated as the reaction product at an NCO/OH equivalent ratio of 0.5:1.0 to 1.0:1.0 of i) a polyol having a functionality of at least 4 and an equivalent weight of at least 200 with ii) a compound containing urea, isocyanate and alkoxysilane groups corresponding to the formula I

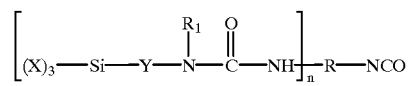

wherein

X represents identical or different organic groups which are inert to isocyanate groups below 100° C., provided that at least one of these groups is an alkoxy group, Y represents a linear or branched alkylene radical containing 1 to 8 carbon atoms, R represents the residue obtained by removing the isocyanate groups from a monomeric polyisocyanate or a polyisocyanate adduct containing n+1 isocyanate groups, $R_1$ represents an organic group which is inert to isocyanate groups at a temperature of 100° C. or less and n is an integer from 1 to 3.

2. The moisture-curable compound of claim 1 wherein said amino compound corresponds to formula IV

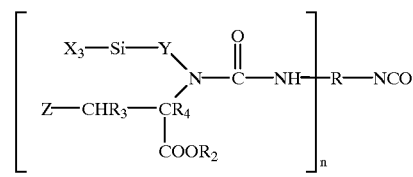

wherein

Z represents $COOR_5$ or an aromatic ring, $R_2$ and $R_5$ are identical or different and represent organic groups which are inert to isocyanate groups at a temperature of 100° C. or less, and $R_3$ and $R_4$ are identical or different and represent hydrogen or organic groups which are inert to isocyanate groups at a temperature of 100° C. or less.

3. The moisture-curable resin of claim 2 wherein

X represents identical or different alkyl or alkoxy groups having 1 to 4 carbon atoms, Y represents a linear alkylene radical containing 2 to 4 carbon atoms, X represents COOR$_5$, R$_2$ and R$_5$ are identical or different and represent alkyl groups having 1 to 9 carbon atoms and R$_3$ and R$_4$ represent hydrogen.

4. The moisture-curable resin of claim 2 wherein

X represents identical or different alkoxy groups having 1 to 4 carbon atoms,

Y represents a linear alkylene radical containing 3 carbon atoms,

Z represents COOR$_5$,

R$_2$ and R$_5$ are identical or different and represent methyl, ethyl or butyl and R$_3$ and R$_4$ represent hydrogen.

5. The moisture-curable resin of claim 1 wherein

R represents the residue obtained by removing the isocyanate groups from a monomeric polyisocyanate having n+1 isocyanate groups and n is 1.

6. The moisture-curable resin of claim 2 wherein

R represents the residue obtained by removing the isocyanate groups from a monomeric polyisocyanate having n+1 isocyanate groups and n is 1.

7. The moisture-curable resin of claim 3 wherein

R represents the residue obtained by removing the isocyanate groups from a monomeric polyisocyanate having n+1 isocyanate groups and n is 1.

8. The moisture-curable resin of claim 4 wherein

R represents the residue obtained by removing the isocyanate groups from a monomeric polyisocyanate having n+1 isocyanate groups and n is 1.

9. A compound containing urea, isocyanate and alkoxysilane groups corresponding to the formula IV

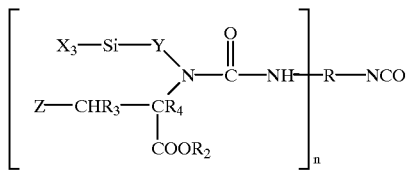

(IV)

wherein

X represents identical or different organic groups which are inert to isocyanate groups below 100° C., provided that at least one of these groups is an alkoxy group, Y represents a linear or branched alkylene radical containing 1 to 8 carbon atoms, Z represents COOR$_5$ or an aromatic ring, R represents the residue obtained by removing the isocyanate groups from a monomeric polyisocyanate or a polyisocyanate adduct containing n+1 isocyanate groups, R$_2$ and R$_5$ are identical or different and represent organic groups which are inert to isocyanate groups at a temperature of 100° C. or less, R$_3$ and R$_4$ are identical or different and represent hydrogen or organic groups which are inert to isocyanate groups at a temperature of 100° C. or less and n is 1 to 2.

10. The compound of claim 9 wherein

X represents identical or different alkyl or alkoxy groups having 1 to 4 carbon atoms, Y represents a linear alkylene radical containing 2 to 4 carbon atoms, Z represents COOR$_5$, R$_2$ and R$_5$ are identical or different and represent alkyl groups having 1 to 9 carbon atoms and R$_3$ and R$_4$ represent hydrogen.

11. The compound of claim 9 wherein

X represents identical or different alkoxy groups having 1 to 4 carbon atoms,

Y represents a linear alkylene radical containing 3 carbon atoms,

Z represents COOR$_5$,

R$_2$ and R$_5$ are identical or different and represent methyl, ethyl or butyl and R$_3$ and R$_4$ represent hydrogen.

12. The compound of claim 9 wherein

R represents the residue obtained by removing the isocyanate groups from a monomeric polyisocyanate having n+1 isocyanate groups and n is 1.

13. The compound of claim 10 wherein

R represents the residue obtained by removing the isocyanate groups from a monomeric polyisocyanate having n+1 isocyanate groups and n is 1.

14. The compound of claim 11 wherein

R represents the residue obtained by removing the isocyanate groups from a monomeric polyisocyanate having n+1 isocyanate groups and n is 1.

15. A process for the preparation of a moisture-curable resin having an alkoxysilane group content (calculated as Si, MW 28) of 0.2 to 4.5% by weight, based on the weight of the moisture-curable resin, and optionally containing hydroxy groups, which comprises reacting at an NCO/OH equivalent ratio of 0.5:1.0 to 1.0:1.0 i) a polyol having a functionality of at least 4 and an equivalent weight of at least 200 with ii) a compound containing urea, isocyanate and alkoxysilane groups corresponding to the formula I $$\left[ (X)_3\text{---Si---Y---N}\underset{\underset{\text{C}}{|}}{\overset{R_1}{|}}\text{---}\overset{O}{\overset{\|}{C}}\text{---NH} \right]_n \text{---R---NCO}$$

(I)

wherein

X represents identical or different organic groups which are inert to isocyanate groups below 100° C., provided that at least one of these groups is an alkoxy group, Y represents a linear or branched alkylene radical containing 1 to 8 carbon atoms, R represents the residue obtained by removing the isocyanate groups from a monomeric polyisocyanate or a polyisocyanate adduct containing n+1 isocyanate groups, R$_1$ represents an organic group which is inert to isocyanate groups at a temperature of 100° C. or less and n is an integer from 1 to 3.

16. The process of claim 15 wherein said amino compound corresponds to formula IV

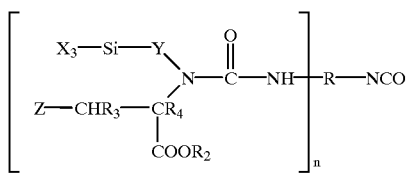

(IV)

wherein
- Z represents $COOR_5$ or an aromatic ring,
- $R_2$ and $R_5$ are identical or different and represent organic groups which are inert to isocyanate groups at a temperature of 100° C. or less, and
- $R_3$ and $R_4$ are identical or different and represent hydrogen or organic groups which are inert to isocyanate groups at a temperature of 100° C. or less.

17. The process of claim 16 wherein
- X represents identical or different alkyl or alkoxy groups having 1 to 4 carbon atoms,
- Y represents a linear alkylene radical containing 2 to 4 carbon atoms,
- Z represents $COOR_5$,
- $R_2$ and $R_5$ are identical or different and represent alkyl groups having 1 to 9 carbon atoms and
- $R_3$ and $R_4$ represent hydrogen.

18. The process of claim 15 wherein
- R represents the residue obtained by removing the isocyanate groups from a monomeric polyisocyanate having n+1 isocyanate groups and
- n is 1.

19. The process of claim 17 wherein
- R represents the residue obtained by removing the isocyanate groups from a monomeric polyisocyanate having n+1 isocyanate groups and
- n is 1.

20. A one-component coating, sealant or adhesive composition wherein the binder comprises the moisture-curable resin of claim 1.

* * * * *